United States Patent [19]

Igarashi et al.

[11] 4,370,475

[45] Jan. 25, 1983

[54] APRAMYCIN DERIVATIVES

[75] Inventors: Kikuo Igarashi, Itami; Tsunetoshi Honma, Ikoma; Tamio Sugawara, Mino, all of Japan

[73] Assignee: Shionogi & Co., Ltd., Osaka, Japan

[21] Appl. No.: 313,969

[22] Filed: Oct. 22, 1981

[30] Foreign Application Priority Data

Oct. 24, 1980 [JP] Japan .............................. 55-149820

[51] Int. Cl.$^3$ ...................... A61K 31/71; C07H 15/22
[52] U.S. Cl. .................................... 536/16.8; 424/180
[58] Field of Search ................................ 536/4, 17 R

[56] References Cited

PUBLICATIONS

O'Connor et al., "Chem. Abst.", vol. 85, 1976, p. 21, 760(t).

*Primary Examiner*—Johnnie R. Brown
*Attorney, Agent, or Firm*—Wenderoth, Lind & Ponack

[57] ABSTRACT

Novel 5,6-dideoxyapramycin derivatives having reinforced antimicrobial activity against gram-positive and negative bacteria with less side effects than apramycin, and produced by sulfonylation of 5- and 6-hydroxy groups and the subsequent reductive removal of sulfonates.

4 Claims, No Drawings

APRAMYCIN DERIVATIVES

BACKGROUND OF THE INVENTION

Chemical modifications of amino glycoside antibiotics have been investigated intensively to reinforce antimicrobial action and reduce side effects. The present inventors have found that the antimicrobial action of apramycin (for example, described as nebramycin factor II in Jap. Patent Publication No. 51-36358) is reinforced remarkably by removal of the 5- and 6-hydroxy groups, and have accomplished this invention.

SUMMARY OF THE INVENTION

The present invention relates to novel 5,6-dideoxyapramycin derivatives represented by the following general formula (I):

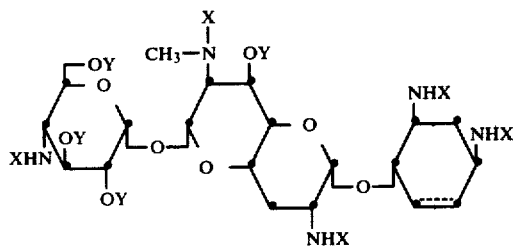

wherein X represents hydrogen or an amino protecting group, Y represents hydrogen or a hydroxy protecting group, and the broken line represents the presence or absence of a double bond.

In the present invention the 5,6-dideoxyapramycin derivatives represented by the general formula (I) include free bases and their salts, and in particular the pharmaceutically acceptable non-toxic acid addition salts. The acids which can form the acid addition salts are inorganic acids, e.g., hydrochloric acid, hydrobromic acid, hydroiodic acid, sulfuric acid, carbonic acid, etc. and organic acids, e.g., acetic acid, fumaric acid, malic acid, tartaric acid, maleic acid, citric acid, mandelic acid, ascorbic acid, gallic acid, etc.

The compounds (I) of the present invention can be produced from apramycin in accordance with the following reaction sequence.

Apramycin can be represented by the following structural formula:

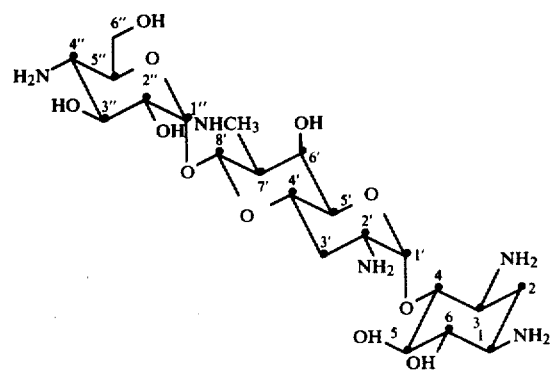

which also shows its conformation more exactly than the simplified formula (II) below which is employed for convenience in the present specification. All of the compounds derived from the compound of formula (II) are also shown in accordance with the more simplified formula.

(Reaction sequence)

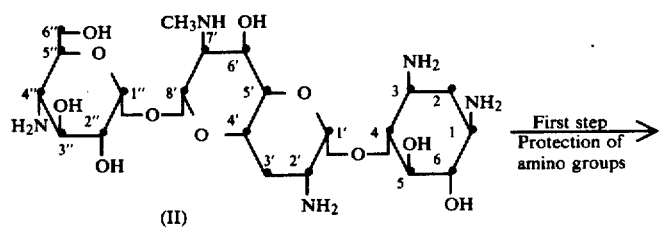

First step
Protection of
amino groups

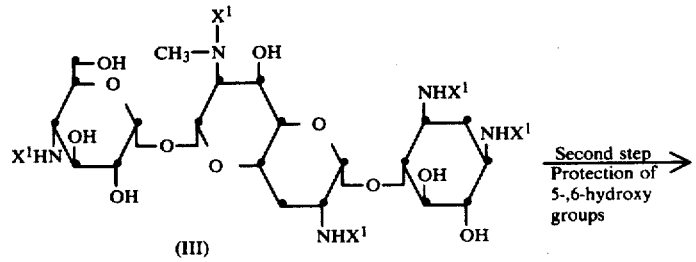

Second step
Protection of
5-,6-hydroxy
groups

-continued
(Reaction sequence)
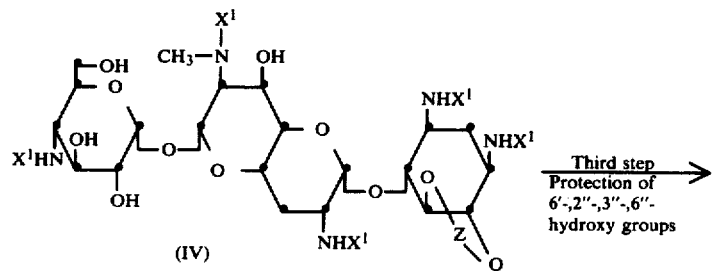
(IV) → Third step
Protection of 6'-,2''-,3''-,6''-hydroxy groups
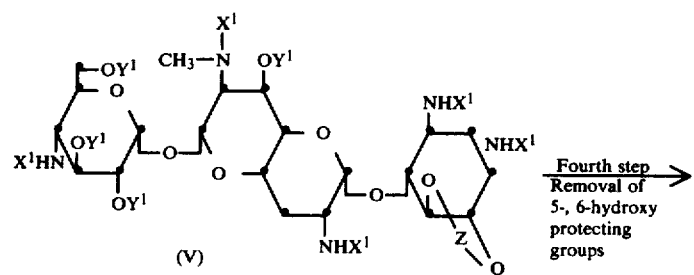
(V) → Fourth step
Removal of 5-, 6-hydroxy protecting groups
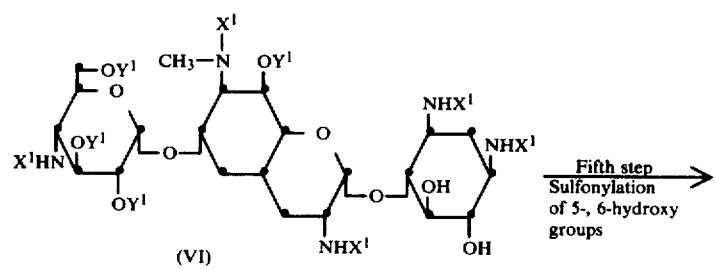
(VI) → Fifth step
Sulfonylation of 5-, 6-hydroxy groups
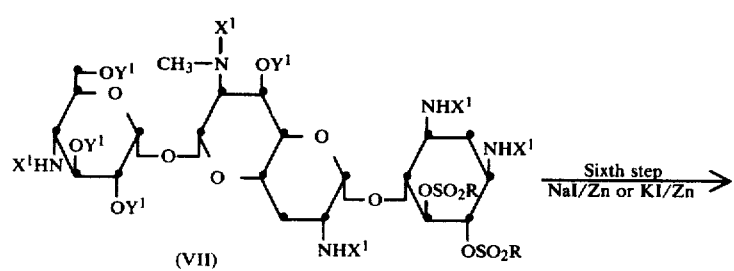
(VII) → Sixth step
NaI/Zn or KI/Zn
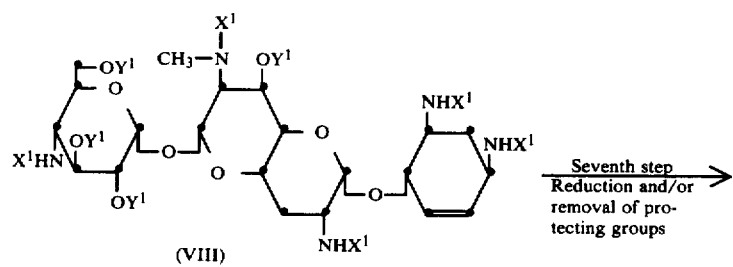
(VIII) → Seventh step
Reduction and/or removal of protecting groups (Reaction sequence)

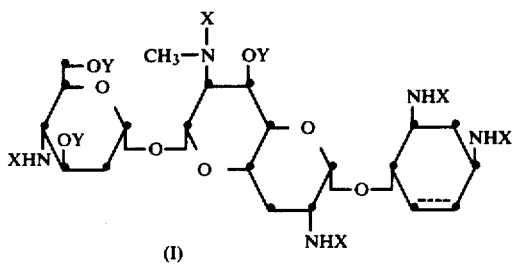

(I)

In these reactions, $X^1$ represents an amino protecting group, $Y^1$ represents a hydroxy protecting group, Z represents a cyclic hydroxy protecting group, $RSO_2$ represents sulfonyl, and X, Y, and the broken line have same meanings as the above.

(The first step)

In this step, the 1-, 3-, 2'-, 7'-, and 4''-amino groups of apramycin are protected. As protecting groups to be introduced, the groups which can easily be removed after termination of the reaction are preferably employed. For example $C_2$–$C_5$ alkanoyl (formyl, acetyl, propanoyl, butanoyl, pentanoyl, etc.), $C_2$–$C_6$ alkoxycarbonyl (methoxycarbonyl, ethoxycarbonyl, propoxycarbonyl, t-butoxycarbonyl, t-amyloxycarbonyl), $C_7$–$C_{10}$ aroyl (benzoyl, phthaloyl, etc.), $C_6$–$C_{10}$ aryloxycarbonyl (phenoxycarbonyl, etc.), $C_7$–$C_{12}$ aralkoxycarbonyl (benzyloxycarbonyl, etc.), m-nitrophenylthio, triphenylthio, and so on are exemplified, and in particular benzyloxycarbonyl is preferred.

The method of introducing protecting groups is known and in case of introducing benzyloxycarbonyl as a protecting group more than 5 equivalents of carbobenzoxychloride may be used in the reaction.

(The second step)

In this step, the 5- and 6-hydroxy groups are protected. As protecting groups the groups which are condensed with 5- and 6-hydroxy groups to form acetals or ketals are preferably employed. For example, ketones such as acetone, methyl ethyl ketone, cyclopentanone, and cyclohexanone, or aldehydes such as acetoaldehyde and propionaldehyde are preferably condensed; in carrying out the reaction, their corresponding dialkylketal or acetals are subjected to the reaction to accomplish the end by means of the known ketal or acetal exchange reaction. Protecting agents are reacted in excess to protect the 2''-, 3''-, and 6''-hydroxy groups at the same time and then the protecting groups introduced at the 2'', 3'', and 6'' positions are removed selectively by hydrolysis with weak acids such as acetic acid to give the 5,6-protected compounds.

This reaction is effected by conventional means in the field of sugar chemistry and may be achieved in proper inert solvents (e.g., benzene, toluene, xylene, dimethylformamide, etc.) in the presence of a catalytic amount of acids (e.g., sulfuric acid, formic acid, p-toluenesulfonic acid, etc.) under anhydrous conditions.

(The third step)

In this step the 6'-, 2''-, 2''-, 3''-, and 6''-hydroxy groups are protected. As protecting groups to be introduced the groups which can easily be removed after termination of the reaction, e.g., acyl groups such as formyl, acetyl, and benzoyl, benzyl, tetrahydropyranyl, etc. are preferred, and the reaction may be carried out in a conventional manner. For example, in case of introducing acetyl more than 4 equivalents of acetic anhydride or acetyl chloride may be used in the reaction.

(The fourth step)

In this step the 5- and 6-protecting groups introduced in the second step are removed, and this may be achieved through hydrolysis in water containing acids, or aqueous methanol, or acetone under mild conditions. As acids inorganic acids such as hydrochloric acid, sulfuric acid, phosphoric acid, etc. and organic acids such as formic acid, acetic acid, etc. can be exemplified, from which a suitable one is chosen preferably according to the kind of protecting groups.

(The fifth step)

In this step the 5- and 6-hydroxy groups are sulfonylated, and as sulfonyls to be introduced $C_1$–$C_4$ alkylsulfonyl [methanesulfonyl (mesyl), ethanesulfonyl, propanesulfonyl, butanesulfonyl, etc.], arylsulfonyl [benzenesulfonyl, p-toluenesulfonyl (tosyl), etc.], or aralkylsulfonyl (benzylsulfonyl, etc.) can be exemplified, and methanesulfonyl (mesyl) is preferred. This reaction can be accomplished on reaction with halides of sulfonyls to be introduced in pyridine or picoline.

(The sixth step)

In proper solvents (dimethylsulfoxide, dimethylformamide, hexametapol, glyme, etc.) the 5,6-disulfonyl compounds (VII) are reacted with sodium iodide or potassium iodide and zinc dust to form a double bond between the 5-carbon atom and the 6-carbon atom along with reductive removal of the sulfonyl [Carbohydrate Research, vol 1, 338–340 (1965)]. The reaction conditions may be in accordance with the known method.

(The seventh step)

This step comprises two steps, one being reduction of the 5-6 double bond and the other being removal of the 1-, 3-, 2'-, 7'-, and 4''-amino protecting groups and the 6'-, 2''-, 3''-, and 6''-hydroxy protecting groups.

Reduction may be conducted by means of so-called catalytic hydrogenation with platinum or palladium-carbon as a catalyst in hydrogen.

In removal of the protecting groups a proper method may be chosen from the known methods according to the kind of protecting groups. If the amino protecting group is benzyloxycarbonyl and the hydroxy protecting group is acetyl, they can be removed concurrently by hydrolysis in the presence of an alkali (sodium hydroxide, potassium hydroxide, etc.).

The reduction in this step affords the compounds of the general formula (I) in which X represents an amino protecting group, Y represents a hydroxy protecting group and the broken line represents the absence of a double bond; the removal reaction of the protecting groups affords the compounds of the general formula (I) in which X and Y represent hydrogen and the broken line represents the presence of a double bond; and the concurrent reduction and removal of the protecting groups afford compounds in which X and Y represent hydrogen and the broken line represents the absence of a double bond.

The following specific compounds can be obtained in accordance with the present invention:

5,6-dideoxyapramycin,

6',2'',3'',6''-tetra-O-acetyl-1,3,2',7',4''-penta-N-benzyloxycarbonyl-5,6-dideoxyapramycin, 5,6-dideoxy-5,6-didehydroapramycin, and 6',2'',3'',6''-tetra-O-acetyl-1,3,2',7',4''-penta-N-benzyloxycarbonyl-5,6-dideoxy-5,6-didehydroapramycin The 5,6-dideoxyapramycin derivatives and their nontoxic salts in the present invention have superior antimicrobial activities and are very effective, not only against sensitive bacteria which are sensitive to apramycin and a recently known potent antibiotic amikacin [Bristol Banyu: 1-N-(4-amino-2-hydroxybutyryl)kanamycin A], but also against resistant bacteria. The following table shows minimum inhibitory concentrations (MIC, $\mu$g/ml) of 5,6-dideoxyapramycin (I: X=Y=H; the broken line is absence of a double bond), apramycin, and amikacin.

| Name of Bacteria | Compound | | |
|---|---|---|---|
| | DDA | APR | AMK |
| Escherichia coli W-677/R5 HL ACC(6')-4 | 3.13 | 6.25 | >100 |
| Escherichia coli AAC (3)-I | 3.13 | 12.5 | 6.25 |
| Escherichia coli W-677/JR762 AAD(2'') | 6.25 | 12.5 | 12.5 |
| Escherichia coli EC-14 | 1.56 | 3.13 | 3.13 |
| Escherichia coli (No.12)EC-159 | 6.25 | 6.25 | 12.5 |
| Escherichia coli (No.2)EC-151 | 3.13 | 6.25 | 100 |
| Proteus inconstans 164 AAC(2') | 6.25 | 25 | 12.5 |
| Proteus inconstans In-15 | 0.39 | 0.78 | 0.78 |
| Proteus rettgeri Ret-11 | 0.78 | 1.56 | 3.13 |
| Proteus rettgeri (No.28)Ret-59 | 0.78 | 1.56 | 1.56 |
| Proteus morganii Morg-74 | 0.78 | 6.25 | 1.56 |
| Proteus morganii Morg-96 | 25 | >100 | 50 |
| Proteus vulgaris CN-329 | 6.25 | 6.25 | 12.5 |
| Proteus mirabilis Pr-4 | 12.5 | 50 | 25 |
| Staphylococcus aureus FDA 209 PJC-1 | 0.39 | 1.56 | 0.78 |
| Staphylococcus aureus ATCC-25923 | 0.78 | 1.56 | 1.56 |
| Staphylococcus aureus S-25 | 0.39 | 1.56 | 3.13 |
| Staphylococcus aureus No.74 | 0.78 | 3.13 | 6.25 |
| Staphylococcus epidermidis ATCC-14990 | 0.2 | 0.39 | 0.39 |
| Staphylococcus epidermidis EP-18 | 0.39 | 0.78 | 1.56 |
| Staphylococcus epidermidis TB-172 | 0.2 | 0.39 | 1.56 |
| Moraxella villon AAC(6')-2 | 1.56 | 6.25 | 25 |
| Klebsiella pneumoniae Kl-184 | 1.56 | 3.13 | 6.25 |
| Klebsiella pneumoniae (No.13)Kl-188 | 1.56 | 3.13 | 25 |
| Pseudomonas aeruginosa TB-151 | 1.56 | 6.25 | 3.13 |
| Pseudomonas aeruginosa TB-166 | 1.56 | 3.13 | 6.25 |
| Serratia marcescens ATCC-13880 | 1.56 | 3.13 | 3.13 |
| Serratia marcescens MA-23 | 1.56 | 6.25 | 25 |
| Serratia marcescens MA-48 | 6.25 | 25 | 25 |
| Serratia marcescens MA-81 | 3.13 | 6.25 | 6.25 |
| Enterobacter cloacae Cl-126 | 0.78 | 3.13 | 1.56 |
| Enterobacter cloacae No.20 | 1.56 | 3.13 | 50 |
| Enterobacter aerogenes AE-16 | 1.56 | 6.25 | 3.13 |
| Enterobacter aerogenes AE-27 | 1.56 | 6.25 | 3.13 |

DDA = 5,6-Dideoxyapramycin  APR = Apramycin  AMK = Amikacin
*Observed in accordance with the standard method for determination of MIC[(1)(2)] regulated by Japan Society of Chemotherapy.
*Wherein the disc for antibiotic sensitivity testing [Modified Mueller Hinton medium (Nissui)] is used as a test medium.
[(1)]Chemotherapy 16(1), 98–99, (1968)
[(2)]Chemotherapy 22(6), 1126–1128, (1974)

As shown in the above table, the compounds (I) of the present invention have antimicrobial activity several times as strong as apramycin, and it is particularly remarkable that the compounds (I) have antimicrobial activities against some kinds of amikacin resistant bacteria several times-several tens' times as strong as amikacin.

Therefore the compounds (I) of the present invention are used for treatment and prevention of various infections caused by a wide variety of gram-positive and gram-negative bacteria, including resistant bacteria. Additionally the compounds (I) of the present invention can be added to perishable foods as a bactericide and moreover as a disinfectant applied to places and implements where bacteria possibly exist.

The compounds (I) of the present invention can be administered to human and other animals orally or parenterally. Particularly, pharmacologically acceptable salts (e.g., sulfate, etc.) can be administered by means of intravenous injection, intramuscular injection, or subcutaneous injection as aqueous solutions. The compounds (I) may be placed in tightly closed ampouls as solutions, preferably preserved in ampouls or vials as crystals, powders, fine crystals, lyophilizate, etc., and dissolved before use. Stabilizer may also be added.

In this connection the compounds (I) together with pharmaceutical components such as diluents (e.g., starch, sucrose, lactose, calcium carbonate, kaolin, etc.), extending agents (e.g., lactose, starch, calcium carbonate, calcium phosphate, kaolin, bentonite, talc, etc.), lubricants (e.g., stearic acid, paraffin, boric acid, silica, sodium benzoate, polyethylene glycol, etc.), and so on, may be formulated into powders, tablets, granules, capsules, troches, dry syrups, suppositories, suspensions, emulsions, inhalants, eye drops, powders for local administration, ointments, etc. and administered. In application for treatment of sensitive infections of humans or animals, the compounds (I) may be administered at a daily dose of 0.01–5 g/kg in injection, preferably 0.02–0.2 g/kg, 0.01–10 g/kg in oral administration, preferably 0.05–0.5 g/kg, and 0.01–10 g/kg in local administration, preferably 0.05–0.5 g/kg, respectively every 3–12 hours. The dosage, however, may be increased or decreased according to sensitivity of pathogenic bacteria, frequency of administration, and the condition of the patient.

The following example will demonstrate the present invention more in detail.

EXAMPLE

5,6-Dideoxyapramycin (a) 1,3,2',7',4''-Penta-N-benzyloxycarbonylapramycin (III: $X^1$=PhCH$_2$OCO)

Apramycin ½ hydrate (10,000 g, 18.23 m mole) is dissolved in water (150 ml), to which sodium carbonate (10.047 g, 94.79 m mole) and acetone (100 ml) are added to give a homogeneous mixture. The mixture is cooled to $-5°$— $-1°$ C., carbobenzoxychloride (14.63 ml, 102.1 m mole) is dropwise added over 15 minutes under vigorous stirring, and after stirring for 2.5 hours at room temperature the reaction mixture is poured into ice water (800 ml). The resultant precipitate is filtered, washed with water, and dissolved in methanol (100 ml), which is evaporated under reduced pressure after decolorization with active carbon (3 g). Ether is added to the obtained residue and the wall of the tube is rubbed with a metal stick. The precipitating powder is filtered, washed with ether, and dried on phosphorus pentoxide under reduced pressure to give the title compound (22.134 g, yield: 100%). A part of this compound is chromatographed on a column [adsorbent: Kiesel gel 60 (made by Merck & Co.); eluent: chloroform-methanol (97:3)], pure fractions are collected, the solvents are evaporated under reduced pressure, and the residue is treated with methanol.ether to give powder.

$[\alpha]_D^{23.0} + 68.1° \pm 1.0°$ (c=1.037, methanol).

IR: $\nu_{max}^{KBr}$ 3406, 1700, 1520 cm$^{-1}$.

Elemental analysis: Calcd. (for $C_{61}H_{71}N_5O_{21}.H_2O$) (%): C, 59.65; H, 5.99; N, 5.70. Found. (%): C, 59.64; H, 5.87; N, 5.70.

(b) 1,3,2',7',4''-Penta-N-benzyloxycarbonyl-5,6-O-cyclohexylideneapramycin (IV: $X^1$=PhCH$_2$OCO,

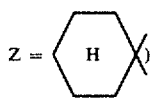

The product from (a) (22.134 g, 18.23 m mole) is dissolved in dimethylformamide (630 ml), cyclohexanone dimethylketal (37 ml, 248.9 m mole) and p-toluenesulfonic acid (2.128 g) are added, and the mixture is stirred under reduced pressure of 25 mm Hg under heating at 50° C. for 3 hours and then neutralized with triethylamine (1.61 ml). The solvent is distilled off under reduced pressure, and the residue (33.1 g) is dissolved in ethyl acetate (300 ml), washed with water, dried on sodium sulfate, and then evaporated under reduced pressure. Thus obtained white powder (25.13 g) is dissolved in 80% acetic acid (210 ml), kept at room temperature for 45 minutes, and then poured in ice water (1 L). The resultant precipitate is filtered, washed with water, and dissolved in ethyl acetate. The mixture is washed with water, dried on sodium sulfate, and evaporated under reduced pressure. The residue (23.60 g) is chromatographed on a column [adsorbent: Kiesel gel 60 (made by Merck & Co.) 800 g; eluent: chloroform∼chloroform-acetone (99:1∼60:40)]. Each fraction is checked by thin layer chromatography, the fractions showing multi-spots are further chromatographed on a column repeatedly in the same manner, and the fractions showing a single spot are collected and crystallized from methanol to give the title compound as a pure product (13.893 g, yield: 59.1%).

mp. 140°–143° C.

$[\alpha]_D^{25} + 63.7° \pm 1.0°$ (c=1.034, ethyl acetate).

IR: $\nu_{max}^{KBr}$ 3400, 1703, 1518 cm$^-$.

Elemental analysis: Calcd. (for $C_{67}H_{79}N_5O_{21}.2H_2O$) (%): C, 60.67; H, 6.31; N, 5.28. Found. (%): C, 60.44; H, 6.09; N, 5.30.

(c) 6',2'',3'',6''-Tetra-O-acetyl-1,3,2',7',4''-penta-N-benzyloxycarbonyl-5,6-O-cyclohexylideneapramycin (V:$X^1$=PhCH$_2$OCO,

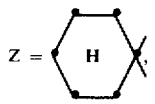

$Y^1$=CH$_3$CO)

The product from (b) (7.000 g, 5.425 m mole) is dissolved in pyridine (91 ml) to which acetic anhydride (20.4 ml) is added, kept at room temperature for 24 hours, and poured in ice water. The precipitate is collected with filtration, washed with water, and dissolved in chloroform, and the mixture is washed with water, dried on sodium sulfate, and evaporated under reduced pressure. The residue (7.80 g) is dissolved in chloroform and hexane is added thereto. The resultant precipitate is filtered to give the title compound (7.345 g, yield: 94.8%).

$[\alpha]_D^{25} + 77.2° \pm 1.1°$ (c=1.079, chloroform).

IR: $\nu_{max}^{KBr}$ 3440, 1745, 1724, 1515 cm$^{-1}$.

Elemental analysis: Calcd. (for $C_{75}H_{87}N_5O_{25}.0.5$-$H_2O$) (%): C, 61.38; H, 6.04; N, 4.77. Found. (%): C, 61.17; H, 5.86; N, 4.71.

(d) 6',2'',3'',6''-Tetra-O-acetyl-1,3,2',7',4''-penta-N-benzyloxycarbonylapramycin (VI: $X^1$=PhCH$_2$OCO, $Y^1$=CH$_3$CO)

The product from (c) (6.000 g, 4.114 m mole) is dissolved in acetic acid (80%, 60 ml) and acetone (30 ml), heated at 70° C. for 6.5 hours, and poured in ice water. The resultant precipitate is filtered, washed with water, and dissolved in ethyl acetate, and the mixture is washed with water, dried on sodium sulfate, and evaporated under reduced pressure. The residue (5.92 g) is dissolved in ethyl acetate and hexane is added thereto. The precipitate (5.60 g) is subjected to liquid chromatography [column: Prepack Column, size C (made by Merck & Co.)] and eluted with benzene-ethyl acetate (1:2) at a rate of 20 ml/fraction. The fractions No. 33–104 are collected, the solvent is evaporated, the obtained residue is dissolved in chloroform, and hexane is added thereto to give the title compound (4.975 g, yield: 87%).

$[\alpha]_D^{25} + 84.2° \pm 1.3°$ (c=1.053, chloroform).

IR: $\nu_{max}^{KBr}$ 3400, 1747, 1724, 1518 cm$^{-1}$.

Elemental analysis Calcd. (for $C_{69}H_{79}N_5O_{25}.H_2O$) (%): C, 59.35; H, 5.85; N, 5.02. Found. (%): C, 59.38; H, 5.61; N, 4.97.

(e) 6',2'',3'',6''-Tetra-O-acetyl-1,3,2',7',4''-penta-N-benzyloxycarbonyl-5,6-di-O-mesylapramycin (VII: $X^1$=PhCH$_2$—OCO, $Y^1$=CH$_3$CO, R=CH$_3$)

The compound from (d) (200 mg, 0.143 m mole) is dissolved in anhydrous pyridine (2 ml) and evaporated to dryness with a vacuum pump under reduced pressure, the residue is dissolved in anhydrous pyridine (2 ml), and methanesulfonyl chloride (0.166 ml, 2.15 m mole) is added thereto. After being kept at room temperature for 15 hours ice water is added, and the mixture is extracted with chloroform, washed with water, 10% hydrochloric acid, water, 5% potassium hydrogen sulfate, water, 5% sodium hydrogen-carbonate and water respectively and dried on sodium sulfate, and then evaporated under reduced pressure. The obtained residue (225 mg) is subjected to liquid chromatography with Prepack Column, size B (made by Merck & Co.) and eluted with benzene-acetone (4:1) (10 ml a fraction, flow rate: 5 ml/min.). The fractions No. 17–33 are collected, and evaporated under reduced pressure, the obtained residue is dissolved in chloroform, and to the mixture hexane is added to give the title compound (217 mg, 97.7%) as precipitate.

$[\alpha]_D^{23.5} + 58.6° \pm 1.0°$ (c=1.027, chloroform).

IR: $\nu_{max}^{CHCl_3}$ 3390, 1743, 1719, 1518, 1349, 1175 cm$^{-1}$.

Elemental analysis (for $C_{71}H_{83}N_5O_{29}S_2 \cdot H_2O$): Calcd. (%): C, 54.92; H, 5.52; N, 4.51; S, 4.13. Found. (%): C, 54.86; H, 5.24; N, 4.42; S, 4.11.

(f)
6',2'',3'',6''-Tetra-O-acetyl-1,3,2',7',4''-penta-N-benzyloxycarbonyl-5,6-dideoxy-5,6-didehydroapramycin (VIII: $X^1$=PhCH$_2$OCO, $Y^1$=CH$_3$CO)

The product from (e) (217 mg, 0.14 m mole) is dissolved in dimethylformamide (8.5 ml), sodium iodide (2.17 g) and zinc dust (1.09 g) are added, and the mixture is stirred under heating at 100° C. Two hours later the mixture is cooled to room temperature, chloroform is added, insoluble material is filtered and washed with chloroform, the filtrate and the washing are combined, washed with 5% sodium hydrogen carbonate, water, sodium thiosulfate solution, and water respectively, and dried on sodium sulfate, and then evaporated under reduced pressure. The obtained residue (194 mg) is subjected to liquid chromatography with Prepack Column, size B (made by Merck & Co.) and eluted with benzene-acetone (5:1) (10 ml a fraction, flow rate: 5 ml/min.). The fractions No. 27–47 are collected and evaporated under reduced pressure, and the obtained residue (164 mg) is recrystallized from methylene chloride-methanol to give the title compound (137 mg, yield: 72.1%) as prisms.

mp. 180.5°–182° C.

$[\alpha]_D^{23.5} = 135.5° \pm 1.7°$ (c=1.009, chloroform).

IR: $\nu_{max}^{Nujol}$ 3370, 1751, 1723, 1703, 1525 cm$^{-1}$.

Elemental analysis (for $C_{69}H_{77}N_5O_{23} \cdot H_2O$): Calcd. (%): C, 60.83; H, 5.84; N, 5.14. Found. (%): C, 60.65; H, 5.54; N, 5.14.

NMR: $\delta_{ppm}^{CDCl_3:CD_3OD(1:5)}$ 7.30 (s, Ph), 5.55 (broad s, H$_5$, H$_6$), 5.08 (s, PhCH$_2$), 2.93 (s,NCH$_3$), 2.08, 2.00, 184 (s,Ac).

(g) 5,6-Dideoxyapramycin (I: X=Y=H, the broken line represents the absence of a double bond)

The product from (f) (250 mg, 0.184 m mole) is dissolved in methanol (8 ml), 10% palladium-carbon (50 mg) and 2 N-hydrochloric acid (0.46 ml) are added, and catalytic hydrogenation is conducted in H$_2$ gas at 4 atm. Seven hours later 10% palladium-carbon (50 mg) and 2 N-hydrochloric acid (0.23 ml) are further added, and catalytic hydrogenation is conducted again in H$_2$ gas at 4 atm. Four hours later the catalyst is filtered off and washed with aqueous methanol, the filtrate and the washing are combined and neutralized with an ion exchange resin Amberlite IR-45 (OH-type), the resin is filtered off and washed with aqueous methanol, the filtrate and the washing are combined, and the solvent is evaporated to dryness under reduced pressure to give the residue (137 mg).

The above compound (137 mg) is dissolved in water (3 ml), added to 2 N-sodium hydroxide (1.96 ml) at 100° C. under stirring, and refluxed for 4 hours. The mixture is neutralized with 2 N-hydrochloric acid, adsorbed on an ion exchange resin Amberlite CG-50 (NH$_4$+-type, 50 ml), washed with water (250 ml), and eluted with water (1 L) and 0.4 N-ammonium hydroxide (1 L) by means of gradient method (11 ml a fraction). Fractions No. 91–121 are collected and evaporated to dryness under reduced pressure, the obtained residue (94 mg) is dissolved in water (3 ml), 0.1 N-sulfuric acid (7.25 ml) is added, the mixture is adjusted at pH 4.5 and condensed to 1 ml under reduced pressure, ethanol (16 ml) is added thereto, and the resultant precipitate is filtered and washed with ethanol. This precipitate is dissolved in water, active carbon (15 mg) is added, filtered with a glass filter (made by Millipore & Co.) 30 minutes later, and washed with water, and the filtrate and the washing are combined and lyophilized. The obtained residue is kept in a desiccator containing sodium bromide (200 g) and water (100 g) until the residue absorbs moisture and becomes constant weight to give 5,6-dideoxyapramycin sulfate (129 mg, yield: 75.4%).

$[\alpha]_D^{24} + 106.4° \pm 1.4°$ (c=1.041, water).

Elemental analysis (for $C_{21}H_{41}N_5O_9 \cdot 2.5H_2SO_4 \cdot 10H_2O$): Calcd. (%): C, 27.03; H, 7.13; N, 7.51; S, 8.59. Found. (%): C, 27.00; H, 7.11; N, 7.63; S, 8.76

NMR (ppm from the external standard in heavy water): $\delta_{ppm}^{D_2O}$ 6.06 (d, H$_1$' or H$_1$'' J=4 Hz), 5.99 (d, H$_1$'' or H$_1$' J=4 Hz), 5.79 (d, H$_8$', J=8 Hz), 3.45 (s, N—CH$_3$)

What is claimed is:
1. An apramycin derivative of the formula

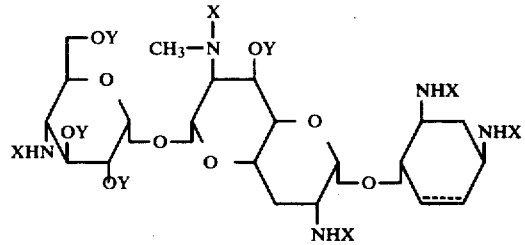

wherein X represents hydrogen or an amino protecting group selected from the group consisting of C$_2$–C$_5$ alkanoyl, C$_2$–C$_6$ alkoxycarbonyl, C$_7$–C$_{10}$ aroyl, C$_6$–C$_{10}$ aryloxycarbonyl, C$_7$–C$_{12}$ aralkoxycarbonyl, m-nitrophenylthio, and triphenylthio; Y represents hydrogen or a hydroxy protecting group selected from the group consisting of formyl, acetyl, benzoyl, benzyl, and tetrahydropyranyl; and the broken line represents the presence or absence of a double bond, or a pharmaceutically acceptable acid addition salt thereof.

2. An apramycin derivative claimed in claim 1, wherein the amino protecting group is benzyloxycarbonyl.

3. An apramycin derivative claimed in claim 1, wherein the hydroxy protecting group is acetyl.

4. 5,6-Dideoxyapramycin.

* * * * *